United States Patent [19]

Gough

[11] 4,382,815
[45] May 10, 1983

[54] 5-[2-CHLORO-4-(TRIFLUOROMETHYL)-PHENOXY]-2-NITROBENZOYL DERIVATIVES OF IMINO-DITHIOLANES

[75] Inventor: Stanley T. D. Gough, Whitehouse Station, N.J.

[73] Assignee: Rhone-Poulenc Agrochimie, Lyons, France

[21] Appl. No.: 287,349

[22] Filed: Jul. 27, 1981

[51] Int. Cl.³ .................... A01N 43/28; A01N 43/32; C07D 339/06; C07D 339/08
[52] U.S. Cl. ....................................... 71/90; 544/238; 546/268; 546/284; 549/38; 549/89
[58] Field of Search ................... 549/38, 89; 546/268, 546/284; 544/238; 71/90

[56] References Cited

U.S. PATENT DOCUMENTS 3,784,635  1/1974  Theissen .......................... 71/98 X
4,063,929  12/1977 Bayer et al. ........................ 71/115
4,307,238  12/1981 Bollinger ............................ 549/38

FOREIGN PATENT DOCUMENTS 13660  7/1980  European Pat. Off. .
30676  6/1981  European Pat. Off. .

Primary Examiner—Richard Raymond
Attorney, Agent, or Firm—Morgan, Finnegan, Pine, Foley & Lee

[57] ABSTRACT

There are provided herbicidal 5-[2-chloro-4-(trifluoromethyl)phenoxy]-2-nitrobenzoyl derivatives of imino-dithiolanes.

6 Claims, No Drawings

5-[2-CHLORO-4-(TRIFLUOROMETHYL)PHENOXY]-2-NITROBENZOYL DERIVATIVES OF IMINO-DITHIOLANES

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Patents which describe such compounds and the like include U.S. Pat. Nos. 3,652,645; 3,784,635; 3,873,302; 3,983,168; 3,907,866; 3,798,276; 3,928,416; and 4,063,929.

SUMMARY OF THE INVENTION

This invention provides certain herbicidal compounds of the formula:

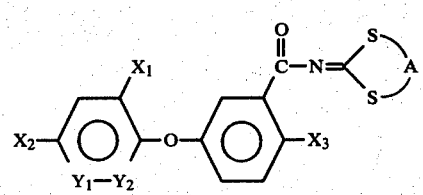

where:
(i) A is an alkylene group having 1 or 2 ring carbon atoms which may further be substituted with one or more alkyl groups having 1 to 4 carbon atoms;
(ii) $Y_1$ is N or C—H;
(iii) $Y_2$ is N or C—$X_4$; provided that $Y_2$ is not C—$X_4$ when $Y_1$ is N; and
(iv) $X_1$, $X_2$, $X_3$ and $X_4$ are groups which are capable of being incorporated into formula I and which collectively impart herbicidal activity thereto.

More particularly, the group A may be represented by the formulae

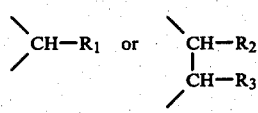

where $R_1$, $R_2$ and $R_3$ ($R_2$ and $R_3$ being the same or different) are H or $C_1$-$C_4$ alkyl.

Examples of the groups $X_1$, $X_2$ and $X_3$ include, e.g., halogen (e.g., Cl, Br or F), polyhaloalkyl (e.g., $CF_3$), $NO_2$, CN, alkyl (e.g., $C_1$-$C_4$ alkyl), $SO_2$ alkyl (e.g., having from 1 to 4 carbon atoms), $SO_2NH_2$, NO, COO alkyl (e.g., having from 2 to 5 carbon atoms), etc. Examples of the group $X_4$ include hydrogen and the examples of groups specified above with respect to $X_1$, $X_2$ and $X_3$. Preferably $X_4$ is H or Cl.

A preferred form of formula I is represented by the formula

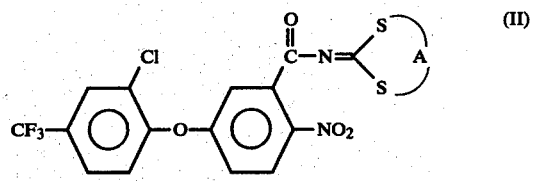

Particular examples of compounds according to formulae I and II include

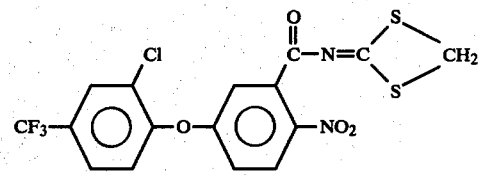

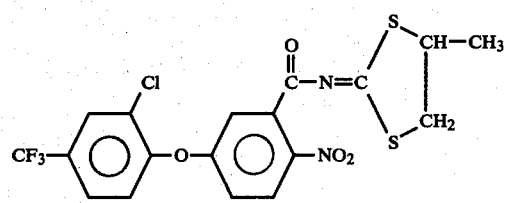

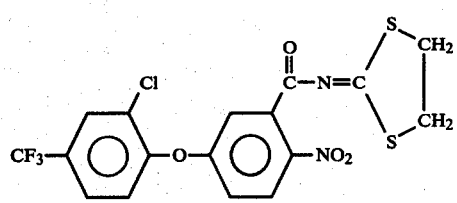

A preferred compound according to Formula I is:

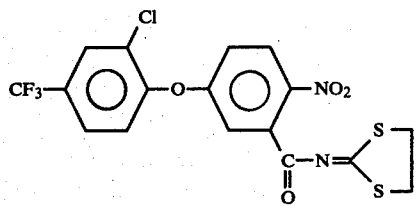

EXAMPLE

Preparation of N-5[2-chloro-4-(trifluoromethyl)-phenoxy]-2-nitrobenzoyl-2-imino-1,3-dithiolane

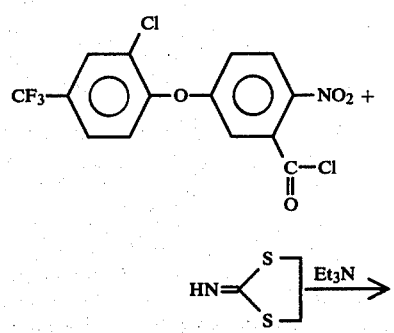

-continued

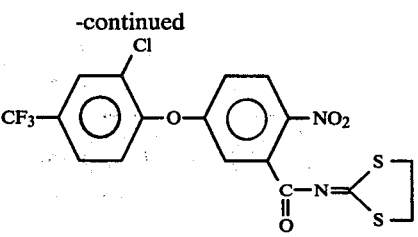

5-[2-chloro-4-(trifluoromethyl)phenoxy]-2-nitrobenzoyl chloride (3.8 g) in toluene (50 ml) is added to a solution of 2-imino-1,3-dithiolane (1.2 g) in toluene (50 ml) containing triethylamine (1.7 g). The mixture is refluxed overnight, then filtered and the solution washed with water, dried and evaporated to give the product.

The compounds of formula I may be prepared by the reaction

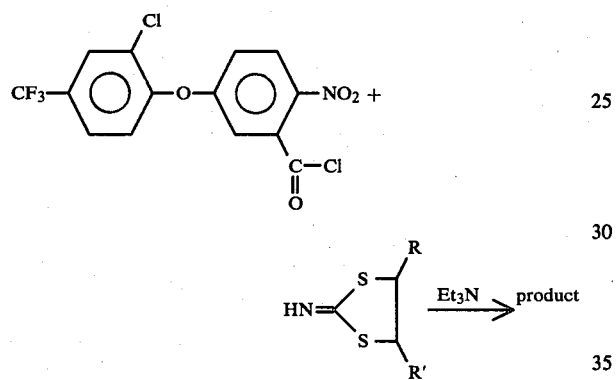

The imino-dithiolanes may be prepared by known methods, e.g.

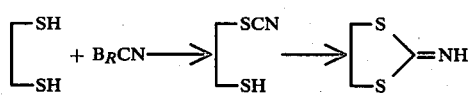

The compounds of this invention can be applied in various ways to achieve herbicidal action. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice, herbicidal application is measured in terms of pounds of herbicide applied per acre. The compounds of this invention are effective herbicides when applied in herbicidal amounts, e.g., at rates between about 0.03 pound and about 10 pounds per acre.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula

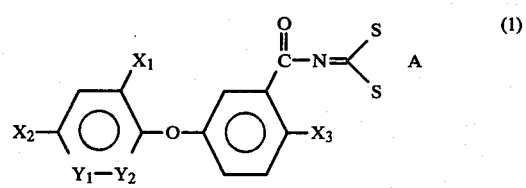

where:
(i) A is an alkylene group having 1 or 2 ring carbon atoms which may further be substituted with one or more alkyl groups having 1 to 4 carbon atoms;
(ii) $Y_1$ is N or C—H;
(iii) $Y_2$ is N or C—$X_4$, provided that $Y_2$ is not C—$X_4$ when $Y_1$ is N;
(iv) $X_1$, $X_2$ and $X_3$ are the same or different and are halogen, polyhaloalkyl, $NO_2$, CN, $C_1$ to $C_4$ alkyl, $SO_2$ alkyl of 1 to 4 carbon atoms, $SO_2NH_2$, NO, and COO alkyl of 2 to 5 carbon atoms; and
(v) $X_4$ is hydrogen or one of the groups specified in part (iv) above with respect to $X_1$, $X_2$ and $X_3$.

2. A compound of the formula

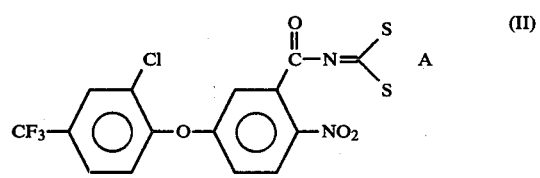

capable of herbicidal activity.

3. A compound selected from the group consisting of

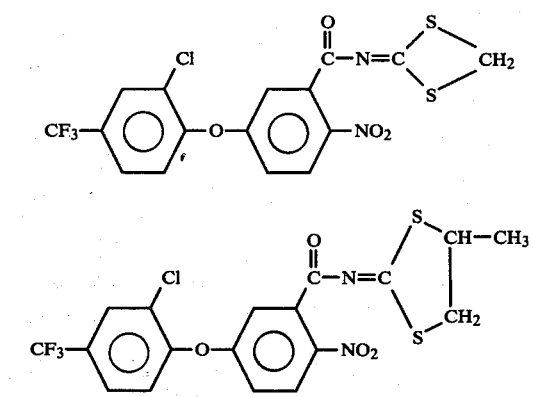

-continued

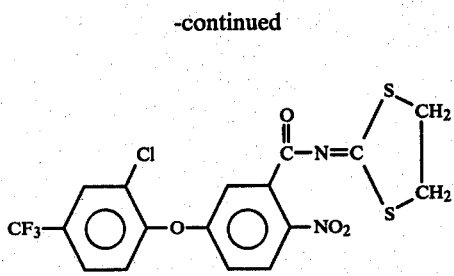

capable of herbicidal activity.

4. A compound of the formula

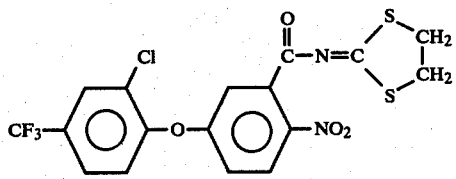

capable of herbicidal activity.

5. A herbicidal composition comprising a herbicidally effective amount of a compound according to any one of claims 1 to 4 and an agronomically acceptable carrier.

6. A method for combating unwanted plants which comprises contacting them with a herbicidally effective amount of a compound according to anyone of claims 1 to 4.

* * * * *

UNITED STATES PATENT AND TRADEMARK OFFICE
CERTIFICATE OF CORRECTION

PATENT NO. : 4,382,815
DATED : May 10, 1983
INVENTOR(S) : Stanley T. D. Gough

It is certified that error appears in the above-identified patent and that said Letters Patent is hereby corrected as shown below:

Claim 1, column 4, lines 15-21, the formula should read as follows:

(I)

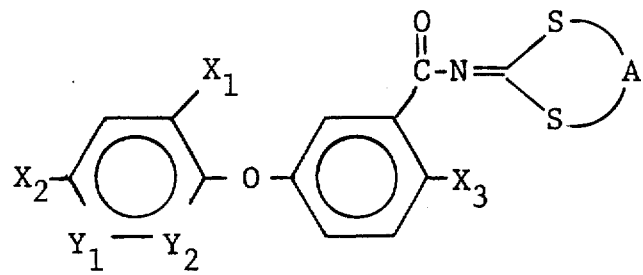

UNITED STATES PATENT AND TRADEMARK OFFICE
CERTIFICATE OF CORRECTION

PATENT NO. : 4,382,815
DATED : May 10, 1983
INVENTOR(S) : Stanley T. D. Gough

It is certified that error appears in the above-identified patent and that said Letters Patent is hereby corrected as shown below:

Claim 2, column 4, lines 40-48, the formula should read as follows:

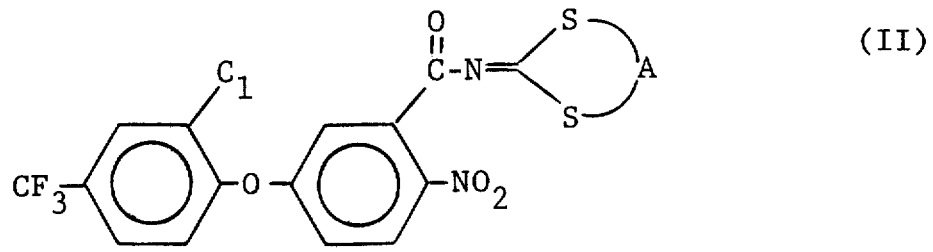

(II)

Signed and Sealed this

Ninth Day of August 1983

[SEAL]

Attest:

GERALD J. MOSSINGHOFF

Attesting Officer      Commissioner of Patents and Trademarks